(12) United States Patent
Wells et al.

(10) Patent No.: US 7,074,930 B2
(45) Date of Patent: Jul. 11, 2006

(54) AMINE SALTS OF AN INTEGRIN RECEPTOR ANTAGONIST

(75) Inventors: Kenneth M. Wells, Hillsborough, NJ (US); Nobuyoshi Yasuda, Mountainside, NJ (US); Yaling Wang, Westfield, NJ (US)

(73) Assignee: Merck & Co., Inc, Rahway, NJ (US)

( * ) Notice: Subject to any disclaimer, the term of this patent is extended or adjusted under 35 U.S.C. 154(b) by 55 days.

(21) Appl. No.: 10/494,760

(22) PCT Filed: Nov. 1, 2002

(86) PCT No.: PCT/US02/35270

§ 371 (c)(1),
(2), (4) Date: May 3, 2004

(87) PCT Pub. No.: WO03/040143

PCT Pub. Date: May 15, 2003

(65) Prior Publication Data

US 2004/0249158 A1    Dec. 9, 2004

Related U.S. Application Data

(60) Provisional application No. 60/333,019, filed on Nov. 11, 2001.

(51) Int. Cl.
*C07D 471/04* (2006.01)
*A61K 31/44* (2006.01)

(52) U.S. Cl. ...................... 546/122; 514/300

(58) Field of Classification Search ............ 546/122; 514/300
See application file for complete search history.

(56) References Cited

U.S. PATENT DOCUMENTS 3,844,791 A * 10/1974 Bloom et al. ............ 430/338
6,017,926 A * 1/2000 Askew et al. ............ 514/300
6,426,353 B1  7/2002 Arison et al.

* cited by examiner

*Primary Examiner*—Shailendra Kumar
(74) *Attorney, Agent, or Firm*—Patricia A. Shatynski; Mark R. Daniel

(57) ABSTRACT

Amine salts of 3-{2-oxo-3-[3-(5,6,7,8-tetrahydro[1,8]naphthyridin-2-yl)-propyl]imidazolidin-1-yl}-3-(6-methoxy-pyridin-3-yl)propionic acid are potent antagonists of the integrin $\alpha v \beta 3$ receptor and are useful for the prevention and/or treatment of osteoporosis and vascular restenosis, as well as conditions associated with excessive angiogenesis, such as macular degeneration, diabetic retinopathy, atherosclerosis, inflammatory arthritis, cancer, and metastatic tumor growth. The invention also relates to a process for the preparation of the novel salts as well as pharmaceutical compositions containing the salts and methods of using the salts.

28 Claims, 6 Drawing Sheets

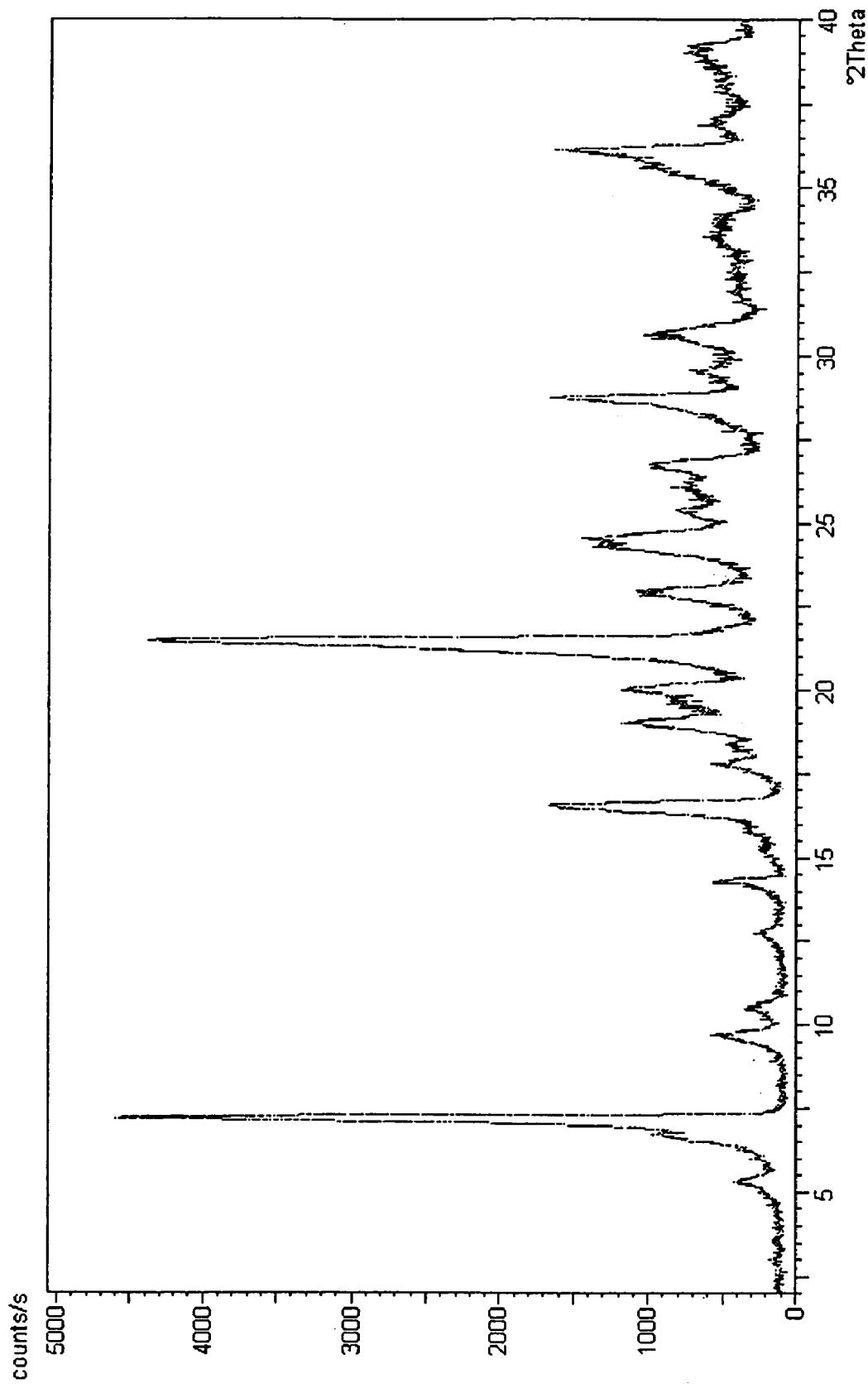
Figure I

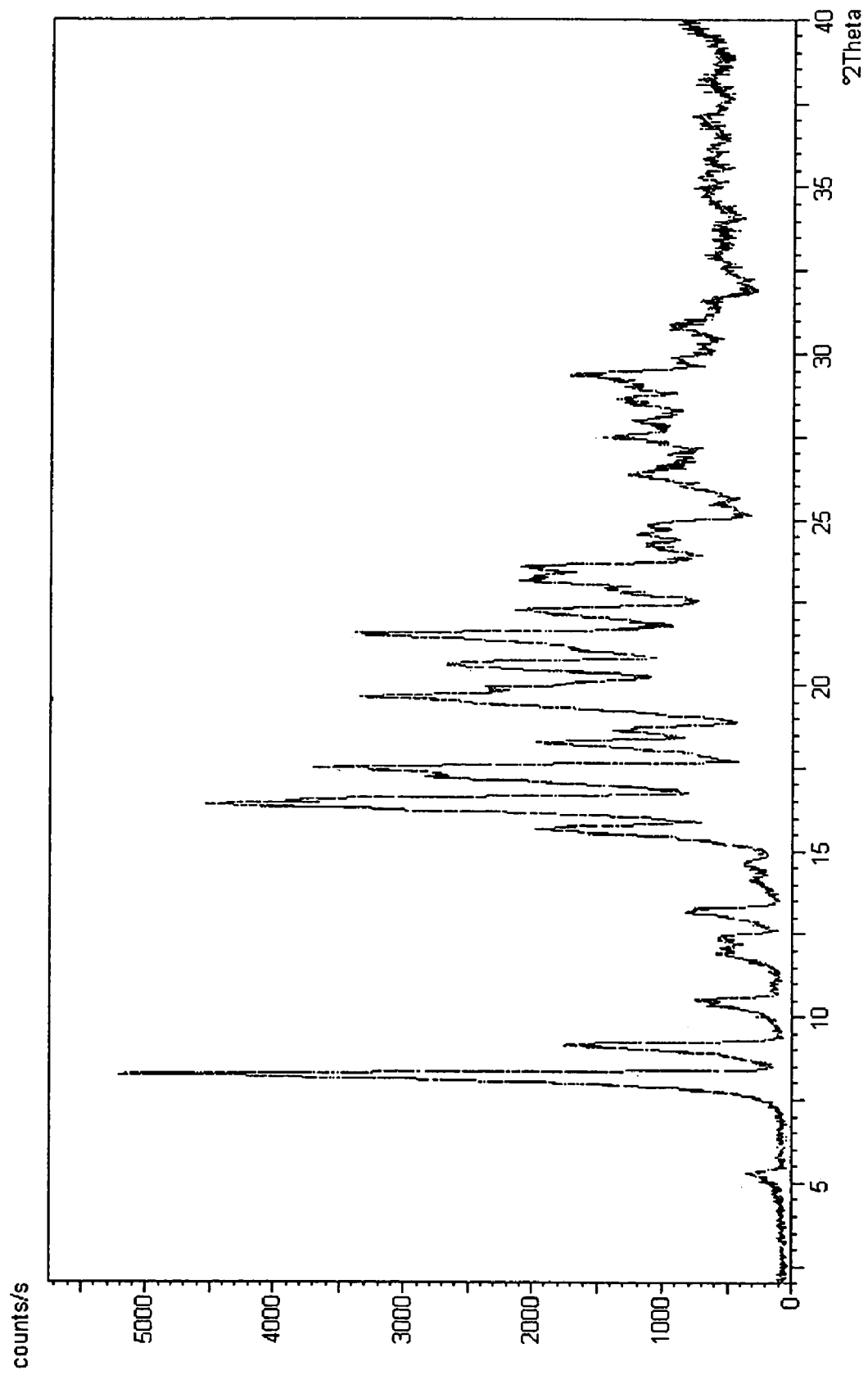
Figure II

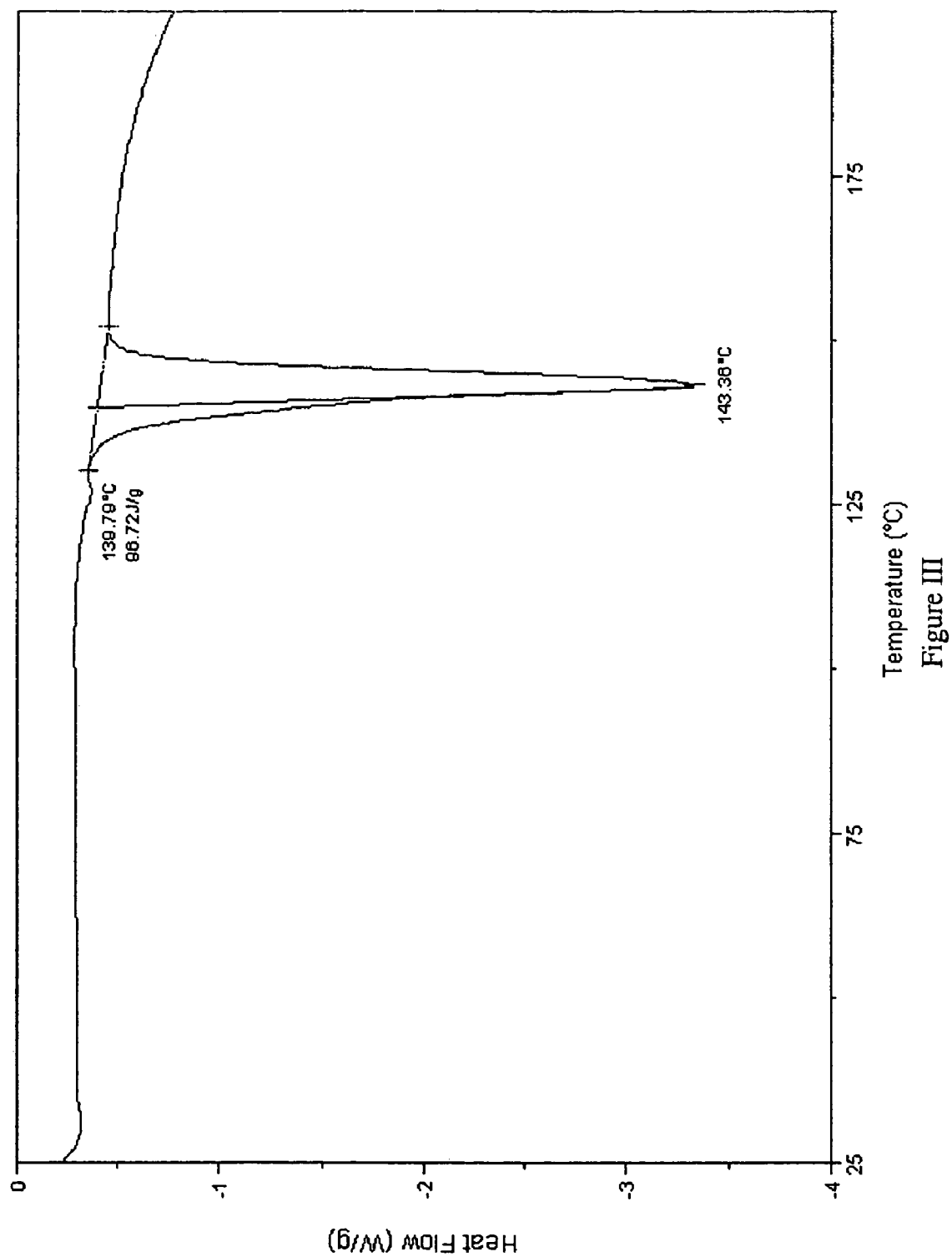
Figure III

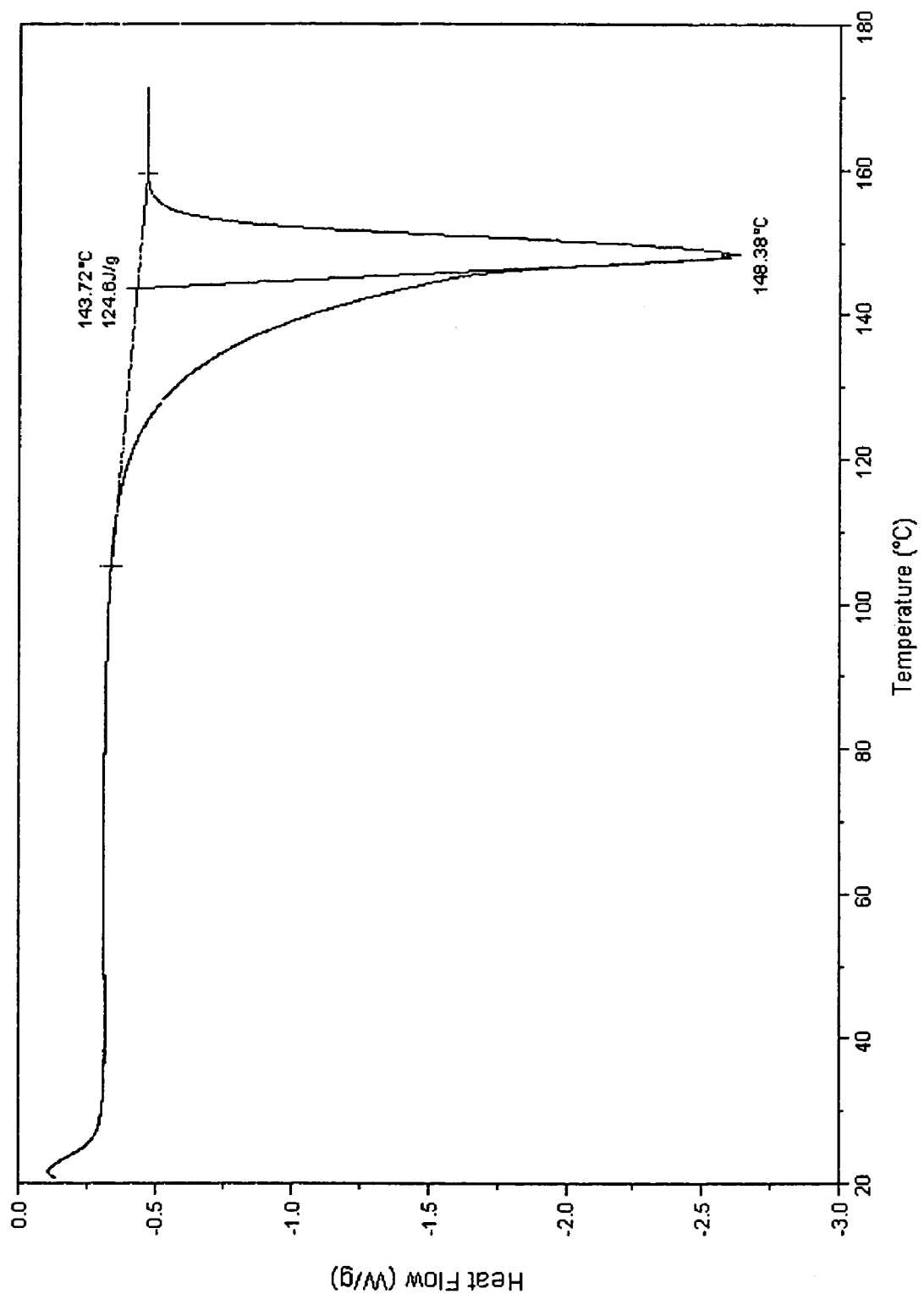
Figure IV

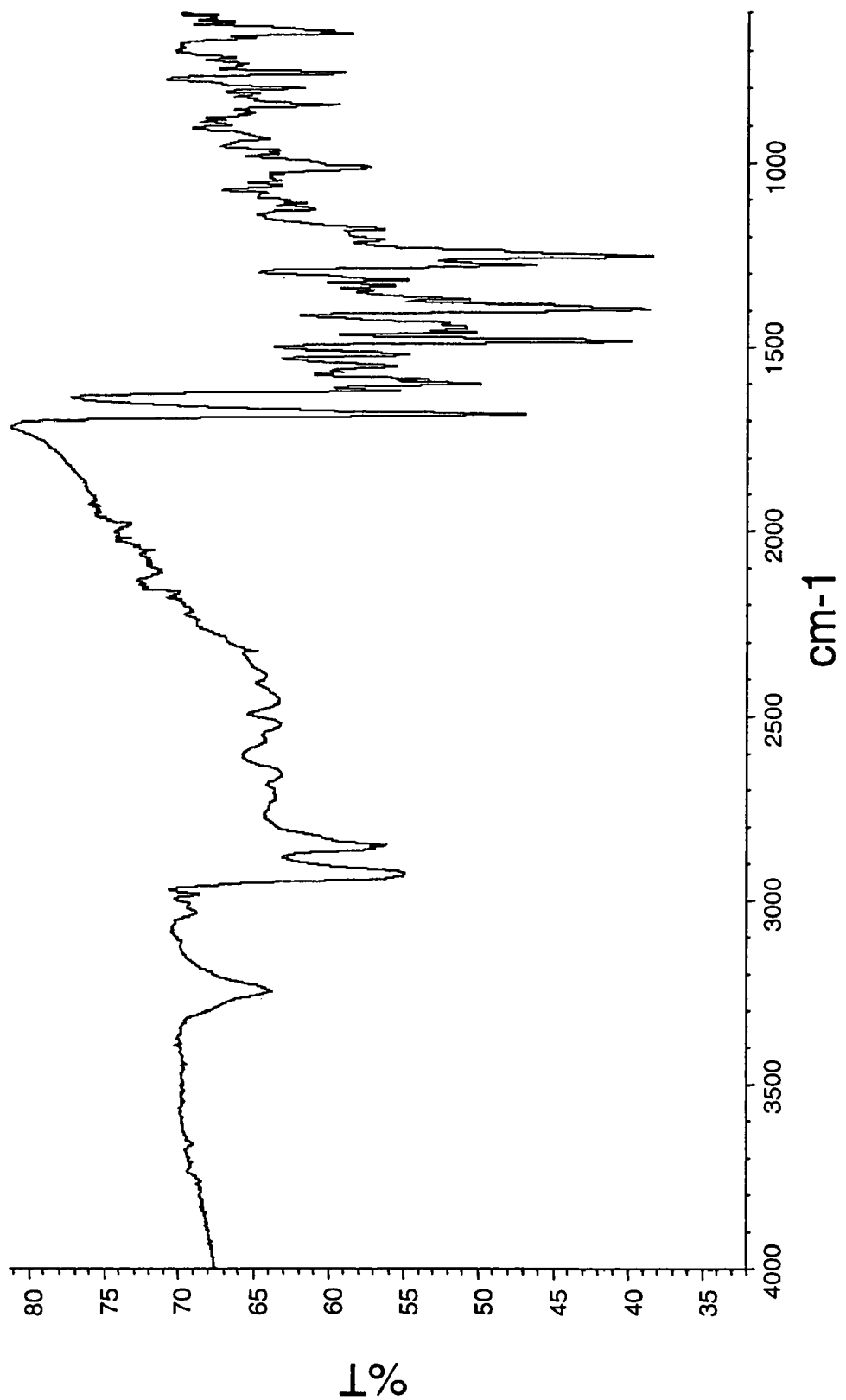
Fig. V

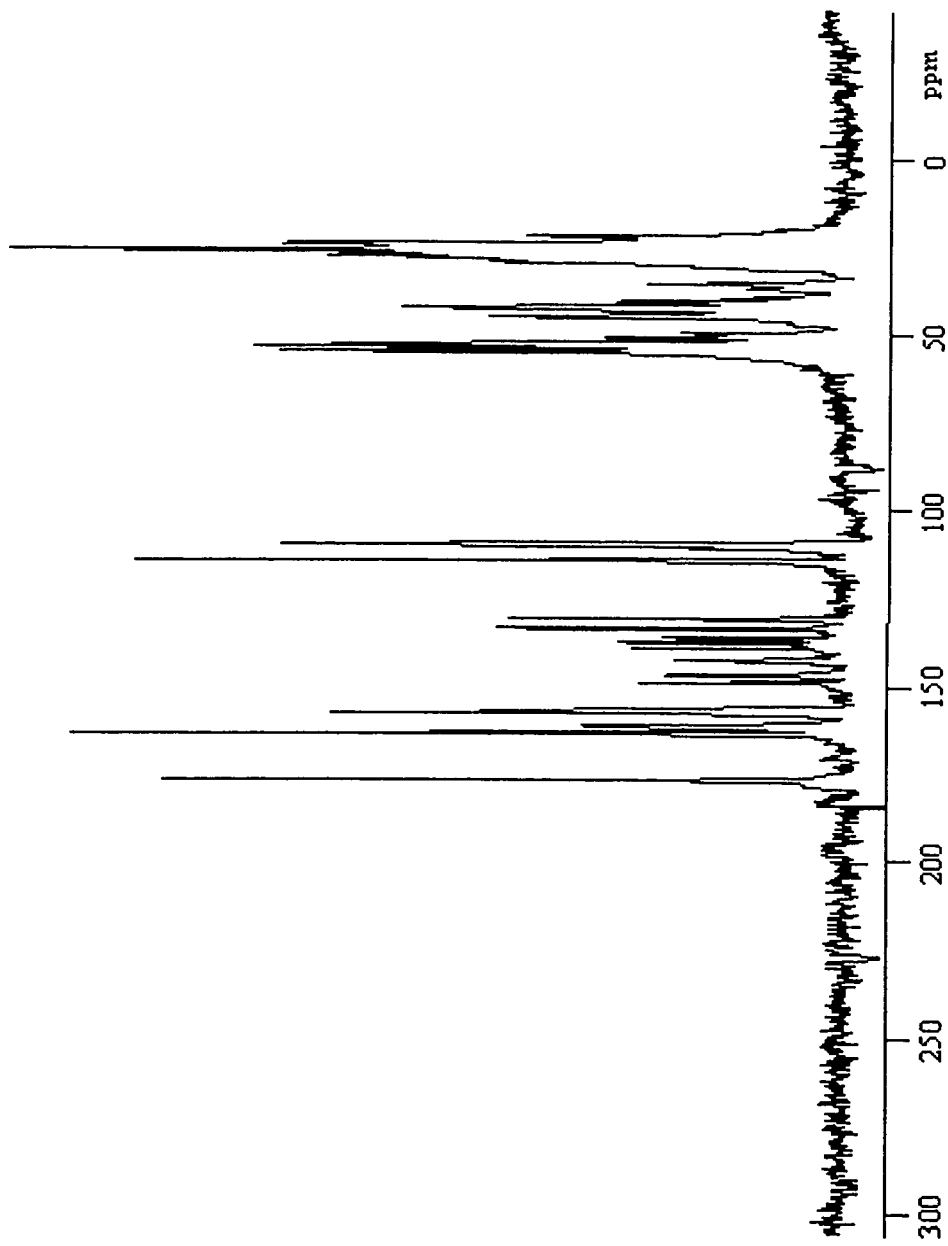
Figure VI

AMINE SALTS OF AN INTEGRIN RECEPTOR ANTAGONIST

This application is a national stage entry under 35 U.S.C.§371 of PCT/US02/35270, filed Nov. 1, 2002, which claims benefit of Provisional Application No. 60/333,019, filed Nov. 11, 2001.

FIELD OF THE INVENTION

The present invention relates to particular salts of an integrin receptor antagonist. More particularly, the invention relates to amine salts of 3-{2-oxo-3-[3-(5,6,7,8-tetrahydro [1,8]naphthyridin-2-yl)propyl]imidazolidin-1-yl}-3-(6-methoxypyridin-3-yl)propionic acid, which are potent integrin $\alpha_v\beta_3$ receptor antagonists. These novel salts are therefore useful for the treatment and prevention of diseases and conditions for which an antagonist of the integrin $\alpha_v\beta_3$ receptor is indicated.

BACKGROUND OF THE INVENTION

Integrin $\alpha_v\beta_3$ receptor antagonists have been described as being of use for the prevention and/or treatment of osteoporosis, vascular restenosis, macular degeneration, diabetic retinopathy, atherosclerosis, inflammatory arthritis, cancer, and metastatic tumor growth see, for example, M. E. Duggan, et al., "Ligands to the integrin receptor $\alpha_v\beta_3$, *Exp. Opin. Ther. Patents,* 10: 1367–1383 (2000); M. Gowen, et al., "Emerging therapies for osteoporosis," *Emerging Drugs,* 5: 1–43 (2000); J. S. Kerr, et al., "Small molecule $\alpha_v$ integrin antagonists: novel anticancer agents," *Exp. Opin. Invest. Drugs,* 9: 1271–1291 (2000); and W. H. Miller, et al., "Identification and in vivo efficacy of small-molecule antagonists of integrin $\alpha_v\beta_3$ (the vitronectin receptor)," *Drug Discovery Today,* 5: 397–408 (2000)].

U.S. Pat. No. 6,017,926, assigned to Merck & Co., describes a class of 2-oxo-imidazolidin-1-yl-propionic acid derivatives, which are potent integrin $\alpha_v\beta_3$ receptor antagonists and therefore useful for inhibiting bone resorption, vascular restenosis, treating and/or preventing osteoporosis, and inhibiting diseases and conditions associated with excessive and undesirable angiogenesis. Specifically disclosed in U.S. Pat. No. 6,017,926 is 3-{2-oxo-3-[3-(5,6,7,8-tetrahydro[1,8]naphthyridin-2-yl)propyl]imidazolidin-1-yl}-3-(6-methoxy-pyridin-3-yl)propionic acid. Pharmaceutically acceptable salts of this compound are generically encompassed within the scope of U.S. Pat. No. 6,017,926.

However, there is no specific disclosure in the above reference of the newly discovered amine salts of 3-{2-oxo-3-[3-(5,6,7,8-tetrahydro[1,8]naphthyridin-2-yl)propyl]imidazolidin-1-yl}-3-(6-methoxy-pyridin-3-yl)propionic acid of structural formula I below of the present invention.

SUMMARY OF THE INVENTION

The present invention provides new amine salts of 3-{2-oxo-3-[3-(5,6,7,8-tetrahydro[1,8]naphthyridin-2-yl)propyl]imidazolidin-1-yl}-3-(6-methoxypyridin-3-yl)propionic acid of the following structural formula I:

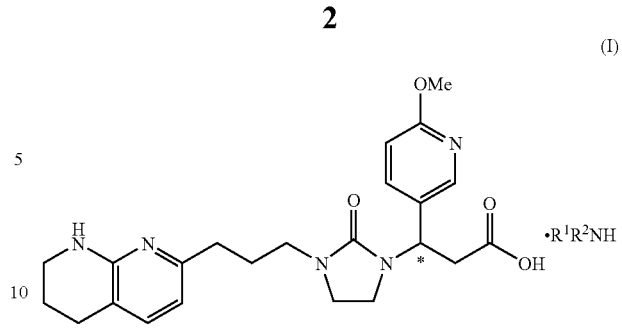

(I)

or a pharmaceutically acceptable solvate, including hydrate, thereof, wherein
$R^1$ is hydrogen and $R^2$ is $C(CH_2OH)_3$;
$R^1$ is hydrogen and $R^2$ is $C(CH_3)_2CH_2OH$; or
$R^1$ and $R^2$ are both cyclohexyl.

The amine salts of the present invention have a chiral center (indicated with an *) at the C-3 position of the propionic acid acid chain and can thus occur as a racemate, racemic mixture, and single enantiomers, with all isomeric forms being included in the present invention. The separate enantiomers, substantially free of the other, are included within the scope of the invention, as well as mixtures of the two enantiomers.

Therefore, one embodiment of the present invention provides the amine salts of 3-{2-oxo-3-[3-(5,6,7,8-tetrahydro [1,8]naphthyridin-2-yl)-propyl]imidazolidin-1-yl}-3(S)-(6-methoxy-pyridin-3-yl)propionic acid of structural formula II:

(II)

wherein
$R^1$ is hydrogen and $R^2$ is $C(CH_2OH)_3$;
$R^1$ is hydrogen and $R^2$ is $C(CH_3)_2CH_2OH$; or
$R^1$ and $R^2$ are both cyclohexyl.

A second embodiment of the present invention provides the amine salts of 3-{2-oxo-3-[3-(5,6,7,8-tetrahydro[1,8] naphthyridin-2-yl)-propyl]imidazolidin-1-yl}-3(R)-(6-methoxy-pyridin-3-yl)propionic acid of structural formula III:

(III)

wherein
$R^1$ is hydrogen and $R^2$ is $C(CH_2OH)_3$;

$R^1$ is hydrogen and $R^2$ is $C(CH_3)_2CH_2OH$; or $R^1$ and $R^2$ are both cyclohexyl.

More specifically, the amine salts of the present invention are comprised of one molar equivalent of 3-{2-oxo-3-[3-(5,6,7,8-tetrahydro[1,8]naphthyridin-2-yl)propyl]imidazolidin-1-yl}-3-(6-methoxy-pyridin-3-yl)propionic acid anion and one molar equivalent of protonated dicyclohexylamine cation ($R^1$=$R^2$=cyclohexyl), protonated 2-amino-2-methyl-1-propanol cation [$R^1$=hydrogen, $R^2$=$C(CH_3)_2CH_2OH$], or protonated tris(hydroxymethyl)aminomethane cation [$R^1$=hydrogen, $R^2$=$C(CH_2OH)_3$].

In a further embodiment of the present invention, the amine salts of structural formulae I–III are crystalline.

The crystalline amine salts of structural formula I exhibit greater chemical and physical stability than the parent zwitterionic compound of structural formula IV below. Of particular note is that the amine salts of the present invention are less hygroscopic than the parent zwitterion. These salts therefore have pharmaceutic advantages over the parent zwitterion for the preparation of solid pharmaceutical dosage forms containing the pharmacologically active ingredient.

The amine salts of the present invention, which exhibit potent integrin $\alpha_v\beta_3$ antagonist activity, are particularly useful for inhibiting bone resorption, treating and/or preventing osteoporosis, and inhibiting vascular restenosis, diabetic retinopathy, macular degeneration, atherosclerosis, inflammatory arthritis, cancer, and metastatic tumor growth.

BRIEF DESCRIPTION OF THE FIGURES

FIG. I is a characteristic X-ray diffraction pattern of the crystalline salt of structural formula I wherein $R^1$ is hydrogen and $R^2$ is $C(CH_2OH)_3$.

FIG. II is a characteristic X-ray diffraction pattern of the crystalline salt of structural formula I wherein $R^1$ and $R^2$ are both cyclohexyl.

FIG. III is a differential scanning calorimetric (DSC) curve of the crystalline salt of Formula I wherein $R^1$ is hydrogen and $R^2$ is $C(CH_2OH)_3$.

FIG. IV is a differential scanning calorimetric (DSC) curve of the crystalline salt of Formula I wherein $R^1$ and $R^2$ are both cyclohexyl.

FIG. V is an FT infrared spectrum (FT-IR) of the crystalline salt of Formula I wherein $R^1$ and $R^2$ are both cyclohexyl.

FIG. VI is a carbon-13 cross-polarization magic-angle spinning (CPMAS) nuclear magnetic resonance (NMR) spectrum of the crystalline salt of structural formula I wherein $R^1$ and $R^2$ are both cyclohexyl.

DETAILED DESCRIPTION OF THE INVENTION

The present invention provides a pharmaceutical composition comprising the amine salts of structural formula I above, or a pharmaceutically acceptable solvate thereof, in association with one or more pharmaceutically acceptable carriers.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remington's Pharmaceutical Sciences*, 17$^{th}$ ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 10 mg to about 400 mg of active ingredient. Intravenously, the most preferred doses will range from about 0.1 to about 10 mg/kg/minute during a constant rate infusion. Advantageously, the salt of the present invention may be administered in a single daily dose, or the total daily dosage may be administered in divided doses of two, three or four times daily. Furthermore, the salt of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the salts herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug component can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

According to a further aspect, the present invention provides a process for the preparation of the amine salts of formula I, which process comprises reacting 3-{2-oxo-3-[3-(5,6,7,8-tetrahydro[1,8]naphthyridin-2-yl)propyl]imidazolidin-1-yl}-3-(6-methoxy-pyridin-3-yl)propionic acid of structural formula IV below:

(IV)

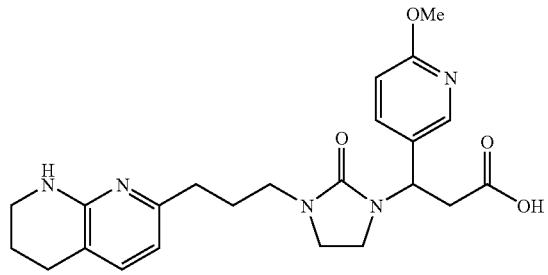

with approximately one molar equivalent of the appropriate amine ($R^1R^2NH$) in a suitable organic solvent. The process is carried out generally at about 0° C. to about 100° C., and preferably at about 20° C. to about 40° C. Generally, the organic solvent is a linear or branched $C_1$–$C_4$ alkanol, such as methanol, ethanol, or isopropanol, a linear or branched $C_{1-4}$ alkyl acetate, such as ethyl acetate or isopropyl acetate, diethyl ether, tetrahydrofuran, toluene, acetone, or acetonitrile. A mixture of water and the organic solvent may also be employed. In one embodiment, the organic solvent is acetonitrile or acetone. Crystallization is then effected by cooling the mixture and optional seeding with crystals of the authentic amine salt, but the latter is not essential. The amine salts are then isolated by filtration and drying. The amine salts are further purified by recrystallization, if necessary.

The starting compound of structural formula IV was prepared by the procedures described in U.S. Pat. No. 6,017,926 or WO 01/34602, the contents of each of which are incorporated by reference in their entirety.

In a still further aspect, the present invention provides a method for the treatment and/or prevention of clinical conditions for which an integrin αvβ3 receptor antagonist is indicated, which method comprises administering to a patient in need of such prevention or treatment a prophylactically or therapeutically effective amount of the salt of structural formula I as defined above or a pharmaceutically acceptable solvate thereof.

The present invention also provides the use of a salt of structural formula I as defined above or pharmaceutically acceptable solvate thereof for the manufacture of a medicament for the prevention and/or treatment of clinical conditions for which an antagonist of the integrin αvβ3 receptor is indicated.

The following non-limiting Examples are intended to illustrate the present invention and should not be construed as being limitations on the scope or spirit of the instant invention.

All X-ray patterns were obtained at ambient conditions on a Philip Analytical X-ray diffractometer with XRG 3100 control and PW 3710 mpd control, using Cu Kα radiation. All DSC thermograms were taken on a TA 2920 Differential Scanning Calorimeter with a heating rate of 10° C./minute under a nitrogen atmosphere in an open pan. The carbon-13 CPMAS nuclear magnetic resonance (NMR) spectra were obtained on a Bruker DSX 400WB NMR spectrometer using a Bruker 7 mm double resonance CPMAS probe while the sample at 7.0 kHz; a contact time of 2.0 milliseconds and a recycle delay of 10 seconds were used for all samples. The carbon-13 spectra is referenced to tetramethylsilane (TMS) using the carbonyl carbon of glycine (176.03 ppm) as a secondary reference. The FT-infrared spectra were measured using a Nicolet Nexus 670 FT-IR spectrometer equipped with the Golden Gate ATR accessory.

EXAMPLE 1

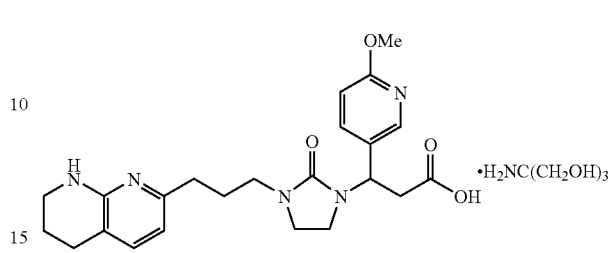

3-{2-Oxo-3-[3-(5,6,7,8-tetrahydro[1,8]naphthyridin-2-yl)-propyl]imidazolidin-1-yl}-3(R or S)-(6-methoxy-pyridin-3-yl)propionic acid tris(hydroxymethyl) aminomethane salt To a warm solution of 3-{2-oxo-3-[3-(5,6,7,8-tetrahydro [1,8]naphthyridin-2-yl)-propyl]imidazolidin-1-yl}-3(R or S)-(6-methoxypyridin-3-yl)propionic acid (5.2 g, 11.8 mmol) in acetonitrile (50 mL) was added tris(hydroxymethyl)aminomethane (1.43 g, 11.8 mmol). The resulting solution was cooled to room temperature. The solid that formed was collected by filtration, washed with acetonitrile (3 mL), and dried under vacuum.

$^1$H NMR ($(CD_3)_2SO$, 400 MHz): δ 8.04 (d, J=2.4 Hz, 1H), 7.56 (dd, J=8.8, 2.4 Hz, 1H), 6.97 (m, 1H), 6.78 (m, 1H), 6.30 (br s, 1H), 6.21 (m, 1H), 5.21 (t, J=7.4 Hz, 1H), 3.78 (s, 3H), 3.42 (m, 6H), 3.29 (q, J=7.4 Hz, 1H), 3.20 (m, 3H), 3.12 (m, 1H), 3.08–2.92 (om, 2H), 2.85 (q, J=8.0 Hz, 1H), 2.69 (q, J=6.8 Hz, 1H), 2.53 (m, 3H), 2.34 (t, J=7.2 Hz, 2H), 1.68 (m, 4H).

$^{13}$C NMR ($(CD_3)_2SO$, 101 MHz): δ 175.2, 163.0, 160.3, 156.9, 156.8, 155.9, 145.9, 138.7, 136.7, 129.4, 113.1, 110.4, 110.3, 60.7, 60.2, 53.4, 51.2, 43.7, 42.5, 41.0, 38.6, 34.5, 27.5, 26.2, 21.2.

The X-ray powder diffraction pattern of the crystalline tris(hydroxymethyl)aminomethane ("tris") salt [$R^1$=H; $R^2$=C(CH$_2$OH)$_3$] is illustrated in FIG. 1. It displayed characteristic diffraction peaks corresponding to d-spacings of 2.5, 3.1, 3.6, 4.1, 4.4, 4.7, 5.3, and 12.2 angstroms.

The differential scanning calorimeter (DSC) curve of the crystalline "tris" salt is illustrated in FIG. III. The DSC curve exhibited a sharp endotherm with a peak temperature of 143° C., an extrapolated onset temperature of 140° C., and an enthalpy of 97 J/g.

Thermogravimetric (TG) analysis obtained at a heating rate of 10° C./min under a nitrogen atmosphere indicated a 0.4% weight loss from room temperature to 155° C.

EXAMPLE 2

3-{2-Oxo-3-[3-(5,6,7,8-tetrahydro[1,8]naphthyridin-2-yl)propyl]imidazolidin-1-yl}-3(S or R)-(6-methoxy-pyridin-3-yl)propionic acid tris(hydroxymethyl) aminomethane salt The enantiomeric "tris" salt was prepared from 3-{2-oxo-3-[3-(5,6,7,8-tetrahydro[1,8]naphthyridin-2-yl)-propyl]imidazolidin-1-yl}-3(S or R)-(6-methoxy-pyridin-3-yl)propionic acid in a similar fashion as that described for Example 1.

EXAMPLE 3

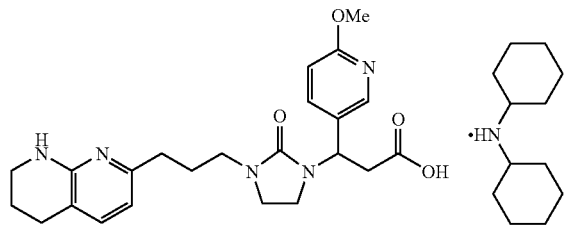

3-{2-Oxo-3-[3-(5,6,7,8-tetrahydro-[1,8]naphthyridin-2-yl)-propyl]imidazolidin-1-yl}-3(R or S)-(6-methoxy-pyridin-3-yl)propionic acid dicyclohexylamine salt To a solution of 3-{2-oxo-3-[3-(5,6,7,8-tetrahydro-[1,8]naphthyridin-2-yl)-propyl]imidazolidin-1-yl}-3(R or S)-(6-methoxy-pyridin-3-yl)-propionic acid (6.0 g, 13.6 mmol) in acetone (100 mL) at 50° C. was added a solution of dicyclohexylamine (2.7 mL, 13.6 mmol) in acetone (20 mL). The resulting solution was cooled to 0° C. The solid that formed was collected by filtration and dried under vacuum.

$^1$H NMR (CD$_3$OD, 400 MHz): δ 8.13 (d, J=2.8 Hz, 1H), 7.69 (dd, J=8.8, 2.8 Hz, 1H), 7.08 (d, J=7.2 Hz, 1H), 6.76 (d, J=9.2 Hz, 1H), 6.35 (d, J=7.2 Hz, 1H), 5.44 (t, J=8.4 Hz, 1H), 3.88 (s, 3H), 3.47 (dt, J=8.8, 6.0 Hz, 1H), 3.36 (t, J=5.6 Hz, 2H), 3.31 (dt, J=3.6, 1.6 Hz, 2H), 3.30–2.95 (om, 6H), 2.81 (dd, J=14.4, 8.8 Hz, 1H), 2.74 (dd, J=14.4, 8.8 Hz, 1H), 2.67 (t, J=6.4 Hz, 2H), 2.58–2.44 (om, 2H), 2.01 (m, 4H), 1.89–1.78 (om, 8H), 1.68 (m, 2H), 1.40–1.10 (om, 10H).

$^{13}$C NMR (CD$_3$OD, 101 MHz): δ 176.9, 163.5, 160.8, 155.7, 155.3, 145.5, 138.3, 137.1, 128.5, 114.2, 110.6, 109.8, 52.8, 52.6, 51.5, 43.0, 42.2, 40.8, 39.2, 38.2, 33.5, 29.4, 27.1, 25.8, 24.8, 24.1, 20.8.

The X-ray powder diffraction pattern of the crystalline dicyclohexylamine salt [R$^1$=R$^2$=cyclohexyl] is illustrated in FIG. II. It displayed characteristic diffraction peaks corresponding to d-spacings of 4.0, 4.1, 4.3, 4.5, 4.9, 5.1, 5.4, 5.7, 9.6, and 10.7 angstroms.

The FT infrared spectrum of the crystalline dicyclohexylamine salt is illustrated in FIG. V, which exhibits significant absorption bands at 3247, 2926, 2849, 1682, 1600, 1552, 1483, 1460, 1396, 1276, 1252, 1014, 762, and 656 cm$^{-1}$.

The crystalline dicyclohexylamine salt was also characterized by solid-state NMR spectroscopy. FIG. VI illustrates the carbon-13 CPMAS NMR spectrum of the crystalline salt which exhibited characteristic signals with chemical shift values of 176.4, 157.4, 157.1, 156.6, 146.5, 142.3, 139.1, 136.1, 133.2, 130.5, 114.2, 109.4, 50.5, 49.3, 44.5, 42.0, 39.0, 35.2, 27.9, 27.1, 24.0, and 21.8 ppm. Further characteristic of the crystalline salt are the signals with chemical shift values of 176.4, 133.2, 130.5, 114.2, 109.4, 42.0, and 35.2 ppm.

The differential scanning calorimeter (DSC) curve of the crystalline dicyclohexylamine salt is illustrated in FIG. 1V. The DSC curve exhibited a sharp endotherm with a peak temperature of 148° C., an extrapolated onset temperature of 144° C., and an enthalpy of 125 J/g. This endotherm was attributed to decomposition of the dicyclohexylamine salt.

Thermogravimetric (TG) analysis obtained at a heating rate of 10° C./min under a nitrogen atmosphere indicated a 0.2% weight loss from room temperature to 94° C., followed by an additional weight loss due to decomposition.

The content of water as obtained with Karl-Fischer titration was 0.1 wt %, indicating that the isolated crystalline dicyclohexylamine salt is an anhydrate.

EXAMPLE 4

3-{2-Oxo-3-[3-(5,6,7,8-tetrahydro-[1,8]naphthyridin-2-yl)-propyl]imidazolidin-1-yl}-(S or R)-(6-methoxy-pyridin-3-yl)propionic acid dicyclohexylamine salt The enantiomeric dicyclohexylamine salt was prepared from 3-{2-oxo-3-[3-(5,6,7,8-tetrahydro-[1,8]naphthyridin-2-yl)-propyl]imidazolidin-1-yl}-3(S or R)-(6-methoxy-pyridin-3-yl)-propionic acid as described for Example 3.

EXAMPLES OF PHARMACEUTICAL FORMULATIONS

The amine salts of formula formula I can be formulated into a tablet by a direct compression process. A 100 mg potency tablet is composed of 100 mg of the active ingredient, 276 mg mannitol, 20 mg of croscarmellose sodium, and 4 mg of magnesium stearate. The active ingredient, microcrystalline cellulose, and croscarmellose are first blended, and the mixture is then lubricated with magnesium stearate and pressed into tablets.

An intravenous (i.v.) aqueous formulation is prepared by dissolving an amine salt of structural formula I in ethanol (10%)/water (90%). For a formulation with a concentration of 5 mg/mL, 5 mg of the active ingredient is dissolved in one mL ethanol (10%)/water (90%) solution.

What is claimed is:

1. A crystalline amine salt of 3-{2-oxo-3-[3-(5,6,7,8-tetrahydro[1,8]naphthyridin-2-yl)propyl]imidazolidin-1-yl}-3-(6-methoxy-pyridin-3-yl)propionic acid of structural formula I:

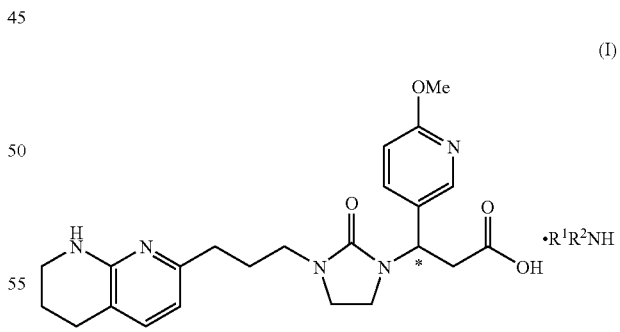

(I)

or a pharmaceutically acceptable solvate, including hydrate, thereof,
wherein
R$^1$ is hydrogen and R$^2$ is C(CH$_2$OH)$_3$;
R$^1$ is hydrogen and R$^2$ is C(CH$_3$)$_2$CH$_2$OH; or
R$^1$ and R$^2$ are both cyclohexyl.

2. The salt of claim 1 of structural formula II having the (S)-configuration at the chiral center marked with an *

(II)

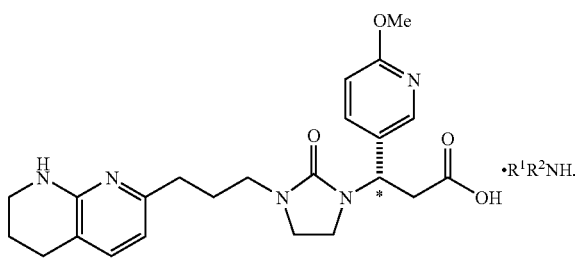

3. The salt of claim 1 of structural formula III having the (R)-configuration at the chiral center marked with an *

(II)

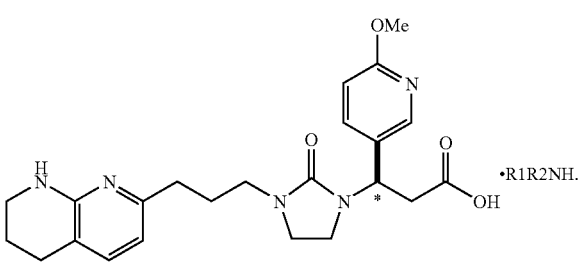

4. The salt of claim 1 wherein $R^1$ is hydrogen and $R^2$ is $C(CH_2OH)_3$.

5. The salt of claim 1 wherein $R^1$ and $R^2$ are both cyclohexyl.

6. The salt of claim 2 wherein $R^1$ is hydrogen and $R^2$ is $C(CH_2OH)_3$ or $R^1$ and $R^2$ are both cyclohexyl.

7. The crystalline salt of claim 4 characterized by an X-ray powder diffraction pattern showing diffraction peaks corresponding to d-spacings of 2.5, 3.1, 3.6, 4.1, 4.4, 4.7, 5.3, and 12.2 angstroms.

8. The crystalline salt of claim 7 characterized by the X-ray powder diffraction pattern of FIG. I.

9. The crystalline salt of claim 4 characterized by the differential scanning calorimetric curve of FIG. III.

10. The crystalline salt of claim 5 characterized by an X-ray powder diffraction pattern showing diffraction peaks corresponding to d-spacings of 4.0, 4.1, 4.3, 4.5, 4.9, 5.1, 5.4, 5.7, 9.6, and 10.7 angstroms.

11. The crystalline salt of claim 10 characterized by the X-ray powder diffraction pattern of FIG. II.

12. The crystalline salt of claim 5 characterized by a solid-state carbon-13 CPMAS nuclear magnetic resonance spectrum showing signals at 176.4, 133.2, 130.5, 114.2, 109.4, 42.0, and 35.2 ppm.

13. The crystalline salt of claim 12 characterized by the solid-state carbon-13 CPMAS nuclear magnetic resonance spectum of FIG. VI.

14. The crystalline salt of claim 5 characterized by the differential scanning calorimetric curve of FIG. IV.

15. The crystalline salt of claim 5 characterized by an FT-infrared spectrum showing absorption bands at 3247, 2926, 2849, 1682, 1600, 1552, 1520, 1483, 1460, 1396, 1276, 1252, 1014, 849, 762, and 656 $cm^{-1}$.

16. The crystalline salt of claim 15 characterized by the FT-infrared spectrum of FIG. V.

17. A salt comprising the ions of 3-{2-oxo-3-[3-(5,6,7,8-tetrahydro[1,8]naphthyridin-2-yl)propyl]imidazolidin-1-yl}-3-(6-methoxy-pyridin-3-yl)propionic acid anion and protonated tris(hydroxymethyl)aminomethane cation.

18. A salt comprising the ions of 3-{2-oxo-3-[3-(5,6,7,8-tetrahydro[1,8]naphthyridin-2-yl)propyl]imidazolidin-1-yl}-3-(6-methoxy-pyridin-3-yl)propionic acid anion and protonated dicyclohexylamine cation.

19. A pharmaceutical composition comprising a prophylactically or therapeutically effective amount of the salt according to claim 1 or a pharmaceutically acceptable solvate thereof in association with one or more pharmaceutically acceptable carriers.

20. A method for the prevention and/or treatment of osteoporosis comprising administering to a patient in need of such prevention or treatment a prophylactically or therapeutically effective amount of the salt according to claim 1, or a pharmaceutically acceptable solvate thereof.

21. A method for the treatment of a disease or condition characterized by excessive angiogenesis comprising administering to a patient in need of such treatment a therapeutically effective amount of the salt according to claim 1, or a pharmaceutically acceptable solvate thereof.

22. The method of claim 21 wherein said disease or condition is selected from the group consisting of macular degeneration, vascular restenosis, diabetic retinopathy, atherosclerosis, and inflammatory arthritis.

23. A process for preparing the amine salt of claim 1 comprising the step of contacting one molar equivalent of 3-{2-oxo-3-[3-(5,6,7,8-tetrahydro[1,8]naphthyridin-2-yl)propyl]imidazolidin-1-yl}-3-(6-methoxy-pyridin-3-yl)propionic acid in an organic solvent or an organic solvent/water mixture with about a one molar equivalent of an amine $R^1R^2NH$ wherein $R^1$ is hydrogen and $R^2$ is $C(CH_2OH)_3$;
$R^1$ is hydrogen and $R^2$ is $C(CH_3)_2CH_2OH$; or
$R^1$ and $R^2$ are both cyclohexyl;

at a temperature in the range of about 0° C. to about 100° C.

24. The process of claim 23 wherein said organic solvent is acetonitrile or acetone.

25. The pharmaceutical composition of claim 19 adapted for i.v. administration.

26. The amine salt of 3-{2-oxo-3-[3-(5,6,7,8-tetrahydro[1,8]naphthyridin-2-yl)propyl]imidazolidin-1-yl}-3(S)-(6-methoxy-pyridin-3-yl)propionic acid prepared according to the process of claim 23.

27. The crystalline salt of claim 4 characterized in being anhydrous.

28. The crystalline salt of claim 5 characterized in being anhydrous.

* * * * *